United States Patent
Okada et al.

(10) Patent No.: US 7,033,800 B2
(45) Date of Patent: Apr. 25, 2006

(54) GLYCOSYL TRANSFER PRODUCT

(75) Inventors: Shigetaka Okada, Ikoma (JP); Takashi Kometani, Itami (JP); Takahisa Nishimura, Nara (JP); Takashi Nakae, Sanda (JP); Hiroshi Takii, Nagaokakyo (JP)

(73) Assignee: Ezaki Glico Co., Ltd., (JP)

( * ) Notice: Subject to any disclaimer, the term of this patent is extended or adjusted under 35 U.S.C. 154(b) by 395 days.

(21) Appl. No.: 10/240,057

(22) PCT Filed: Mar. 28, 2001

(86) PCT No.: PCT/JP01/02601

§ 371 (c)(1),
(2), (4) Date: Sep. 27, 2002

(87) PCT Pub. No.: WO01/73106

PCT Pub. Date: Oct. 4, 2001

(65) Prior Publication Data

US 2003/0082751 A1    May 1, 2003

(30) Foreign Application Priority Data

Mar. 28, 2000  (JP) ............... 2000-89748

(51) Int. Cl.
   *C12P 19/44*   (2006.01)
   *C12N 9/28*    (2006.01)
(52) U.S. Cl. ............ 435/74; 435/200; 435/202
(58) Field of Classification Search ........... 435/74, 435/200, 202
See application file for complete search history.

(56) References Cited

U.S. PATENT DOCUMENTS 5,145,781 A * 9/1992 Suzuki et al. ............ 435/99

FOREIGN PATENT DOCUMENTS

| JP | 05-219947 | 8/1993 |
| JP | 06-277087 | 10/1994 |
| JP | 06-284896 | 10/1994 |
| JP | 08-173183 | 7/1996 |

OTHER PUBLICATIONS

Park et al., "Transglycosylation Reactions of *Bacillus stearothermophilus* Maltogenic Amylase with Acarbose and Various Acceptors," *Carbohydrate Research 313*, (1998) 235-246, Elsevier.
Park et al., "Structure, Specificity and Function of Cyclomaltodextrinase, A Multispecific Enzyme of the α-Amylase Family,"0 *biochimica et Biophysica Acta 1478*, (2000) 165-185, Elsevier.

* cited by examiner

*Primary Examiner*—Herbert J. Lilling
(74) *Attorney, Agent, or Firm*—Fay, Sharpe, Fagan, Minnich & McKee, LLP

(57) ABSTRACT

A method of producing a phenol derivative glycoside is provided. The method comprises the step of allowing a saccharide and a phenol derivative to react with each other in the presence of an enzyme to produce the phenol derivative glycoside. The enzyme is selected from the group consisting of neopullulanase, cyclomaltodextrinase, maltogenic α-amylase, and saccharifying amylase having cyclodextrin synthesizing capability.

9 Claims, No Drawings

SEQUENCE LISTING

```
<160> NUMBER OF SEQ ID NOS: 4

<210> SEQ ID NO 1
<211> LENGTH: 25
<212> TYPE: DNA
<213> ORGANISM: alkalophilic Bacillus sp. strain A2-5a
      (DBJ/EMBL/Genbank; AB015670)

<400> SEQUENCE: 1
tggccatggt aaaagaagcg attta                                           25

<210> SEQ ID NO 2
<211> LENGTH: 30
<212> TYPE: DNA
<213> ORGANISM: alkalophilic Bacillus sp. strain A2-5a
      (DBJ/EMBL/Genbank; AB015670)

<400> SEQUENCE: 2
ttcggtacct taaatcacct ttataacacc                                      30

<210> SEQ ID NO 3
<211> LENGTH: 28
<212> TYPE: DNA
<213> ORGANISM: Bacillus licheniformis

<400> SEQUENCE: 3
tggcatatga tcgaattagc agcgatac                                        28
```

```
<210> SEQ ID NO 4
<211> LENGTH: 28
<212> TYPE: DNA
<213> ORGANISM: Bacillus licheniformis

<400> SEQUENCE: 4
cttgaattct taacagaatt tagaccgc                                    28
```

GLYCOSYL TRANSFER PRODUCT

TECHNICAL FIELD

The present invention relates to a method for producing a phenol derivative glycoside using neopullulanase, cyclomaltodextrinase, maltogenic α-amylase, or saccharifying amylase having cyclodextrin synthesizing capability.

BACKGROUND ART

Phenol derivative glycosides are conventionally used as pigments, sweeteners, analgesics, antioxidants, and the like, and are also used as an ingredient for cosmetics for exhibiting an excellent whitening effect. It is known that glycosylation of a phenol derivative can improve the stability, quality of taste and absorbability of the unglycosylated compound.

The present applicant has provided a method for producing a polyphenol glycoside using saccharifying α-amylase (Japanese Patent No. 2662667 and Japanese Patent No. 2805273) produced by *Bacillus subtilis* strain X-23.

It is also known that a saccharifying amylase not having cyclodextrin synthesizing capability glycosylates polyphenol (Japanese Publication for Opposition No. 7-36758 and J. Ferment. Bioeng., 78:31(1994)). However, When hydroquinone, which is a type of polyphenol, is glycosylated using the conventionally known saccharifying amylase not having cyclodextrin synthesizing capability (Japanese Publication for Opposition No. 7-36758), two glycosides are produced, i.e., hydroquinone-O-α-D-glucopyranoside and hydroquinone-O-α-D-maltoside. The weights of these produced substances are 110 mg and 51 mg, respectively. Thus, conventional methods produce a mixture containing a number of various types of hydroquinone glycosides, causing a problem that the methods require costly purification of a product of interest.

It has been known that some saccharifying amylase derived from *Bacillus subtilis* has cyclodextrin synthesizing capability (J. Ferment. Bioeng., 81:26(1996)). However, it has never been known that the amylase having cyclodextrin synthesizing capability of *Bacillus subtilis* can also glycosylate a phenol derivative.

It has also never been known that neopullulanase, cyclomaltodextrinase, and maltogenic α-amylase can transfer a saccharide to a polyphenol to produce a glycoside.

Another conventionally known glycosylation method is a glycosylation method using cyclodextrin glucanotransferase (Japanese Laid-Open Publication No. 3-7593) which transfers an additional saccharide to a saccharide portion of a polyphenol compound containing a saccharide in the molecule. However, this method cannot efficiently transfer a saccharide to a polyphenol compound not containing a saccharide moiety. A number of phenol derivatives having various physiological activities do not contain a saccharide moiety. There is a demand for an improvement in the stability and absorbability of such phenol derivatives.

In a number of enzyme reactions for producing a glycoside, malto-oligosaccharides, which are obtained as byproducts by the end of the enzyme reaction, have no useful application. Therefore, there is a demand for a phenol derivative glycosylation method which produces a useful byproduct.

Conventionally, ligand exchange chromatography using cation exchange resin is used for separation of saccharides, such as separation of glucose and fructose. In chromatography for purifying glycosides, hydrophobic adsorption resin is generally used.

DISCLOSURE OF THE INVENTION

The present inventors found that neopullulanase, cyclomaltodextrinase, maltogenic α-amylase and saccharifying amylase having cyclodextrin synthesizing capability, which have not substantially been utilized conventionally in industrial fields, have the capability of synthesizing a phenol derivative glycoside, and based on this finding, completed the present invention.

The present inventors found that when a saccharifying amylase having cyclodextrin synthesizing capability is used, a single type of glycoside, i.e., phenol derivative glycoside, is produced by the end of the reaction. If a saccharifying amylase having cyclodextrin synthesizing capability is used to glycosylate hydroquinone, a single type of hydroquinone glycoside, i.e., hydroquinone-O-α-D-glucopyranoside, is produced. Since only one type of product is produced, the glycoside can be purified by an easier method than conventional methods, thereby making it possible to supply high-purity glycoside inexpensively.

The present inventors also found that when neopullulanase, cyclomaltodextrinase, or maltogenic α-amylase is used, phenol derivative glycosides and isomalto-oligosaccharides are produced by the end of the reaction.

The present inventors also found that by glycosylating a phenol derivative, such as catechin-type compounds, caffeic acid, kojic acid, hydroquinone, catechol-type compounds, resorcinol-type compounds, protocatechuic acid, gallic acid, vanillin, daidzein, genistein, α-resorcylic acid, and phloroglucinol, the interaction between the phenol derivative glycosides, and a cation exchange resin, or a metal (e.g., calcium, lead, zinc, and sodium) or hydrogen coupled with cation exchange resin, is different from the interaction between the phenol derivatives and the resins. The present inventors also found that by glycosylating phenol derivatives as described above, the hydrophobic interaction between the phenol derivative glycosides and a portion or the whole of anion exchange resin is different from the interaction between the phenol derivatives and a portion or the whole of anion exchange resin. Based on these findings, the present inventors completed a purification method capable of purifying a glycoside in one step by applying an enzyme reaction product obtained by a glycosylation reaction to column chromatography using cation exchange resin or anion exchange resin.

When neopullulanase, cyclomaltodextrinase, or maltogenic α-amylase is used to produce a phenol derivative glycoside, a large amount of isomalto-oligosaccharides are produced from a substrate which is simultaneously added as a donor. Isomalto-oligosaccharides have received attention as a bifidus factor which enhances growth of beneficial enterobacteria. Therefore, with the method of the present invention, it is possible to obtain phenol derivative glycosides as well as useful byproducts, isomalto-oligosaccharides.

The method of the present invention is characterized in that a saccharide is transferred by the action of the above-described enzymes to a hydroxyl group of a molecule, which acts as a saccharide acceptor, whether or not the molecule contains a saccharide residue. Even when the acceptor molecule contains a saccharide residue, a saccharide is transferred to a hydroxyl group other than that of the saccharide residue. This action is quite different from that of enzymes which are used in conventional methods.

The method of the present invention is a method of producing a phenol derivative glycoside, comprising the step of allowing a saccharide and a phenol derivative to react with each other in the presence of an enzyme to produce the phenol derivative glycoside. The enzyme is selected from the group consisting of neopullulanase, cyclomaltodextrinase, maltogenic α-amylase, and saccharifying amylase having cyclodextrin synthesizing capability.

In one embodiment, the enzyme is neopullulanase. The neopullulanase may be derived from a *bacterium* selected from the group consisting of *Thermoactinomyces vulgaris, Bacteroides thetaiotaomicron, Pseudomonas, Bacillus polymyxa, Bacillus licheniformis, Bacillus stearothermophilus, Bacillus thermoamyloliquefaciens*, and *Thermus thermophilus*.

In one embodiment, the enzyme is cyclomaltodextrinase. The cyclomaltodextrinase may be derived from a *bacterium* selected from the group consisting of *Bacillus stearothermophilus, Bacillus thermophilus, Bacillus coagulanc, Escherichia coli, Flavobacterium, Alkalophilic Bacillus*, and *Bacillus sphaericus*.

In one embodiment, the enzyme is maltogenic α-amylase. The maltogenic α-amylase may be derived from a *bacterium* selected from the group consisting of *Thermoactinomyces vulgaris, Bacteroides thetaiotaomicron, Pseudomonas, Bacillus polymyxa, Bacillus licheniformis, Bacillus stearothermophilus, Bacillus thermoamyloliquefaciens*, and *Thermus thermophilus*.

In one embodiment, the enzyme is a saccharifying amylase having cyclodextrin synthesizing capability. The saccharifying amylase having cyclodextrin synthesizing capability may be derived from a *bacterium* selected from the group consisting of *Bacillus subtilis, Streptococcus bovis, Streptomyces hygroscopicus, Streptomyces praecox, Rhizopus delemar, Aspergillus delemar*, and *Aspergillus niger*.

In one embodiment, the phenol derivative may be selected from the group consisting of flavone-type compounds, isoflavone-type compounds, flavonol-type compounds, flavanone-type compounds, flavanonol-type compounds, catechin-type compounds, aurone-type compounds, chalcone-type compounds, dihydrochalcone-type compounds, kojic acid, dimethoxy phenol, acetaminophen, vanillin, hydroquinone, epigallocatechin, epicatechin gallate, anthocyanidin-type compounds, anthocyanin-type compounds, caffeic acid, catechol, resorcinol, protocatechuic acid, gallic acid, resorcylic acid, and phloroglucinol.

In one embodiment, the saccharide may be selected from the group consisting of malto-oligosaccharides, dextrin, amylose, amylopectin, natural starch, starch degradation products and processed starch.

In one embodiment, the method of the present invention may further comprise the step of using ion exchange resin to fractionate the enzyme reaction products.

In one embodiment, the method of the present invention may further comprise the step of using ion exchange resin to fractionate the enzyme reaction products into at least a fraction containing a byproduct, a fraction containing an unreacted phenol derivative, and a fraction containing a phenol derivative glycoside.

BEST MODE FOR CARRYING OUT THE INVENTION

Hereinafter, the present invention will be described in detail.

The method of the present invention is a method for producing a phenol derivative glycoside.

As used herein, a "phenol derivative glycoside" is a substance in which a phenol derivative moiety is linked to a saccharide moiety with a glycoside linkage. The phenol derivative glycoside may be a mono-glucopyranoside (e.g., hydroquinone-O-α-D-glucopyranoside, caffeic acid-O-α-D-glucopyranoside, 3,4-dimethoxy phenol-O-α-D-glucopyranoside, and catechin-O-α-D-glucopyranoside), a diglucopyranoside or a triglucopyranoside, in which a saccharide moiety(s) is additionally linked to the above-described mono-glucopyranoside, and the like.

The method of the present invention comprises a step of allowing a saccharide and a phenol derivative to react with each other in the presence of an enzyme to form a phenol derivative glycoside.

(1) Saccharide:

As used herein, "saccharides" refer to compounds having the general formula $C_n(H_2O)_m$. Saccharides are grouped into monosaccharides, oligosaccharides, and polysaccharides according to the number of constituents, i.e., saccharide units. In the present invention, oligosaccharides and polysaccharides are preferable. Therefore, n in the above-described general formula is preferably at least 12 and m is preferably at least 11.

An example of a monosaccharide is D-glucose.

As used herein, oligosaccharides refer to substances obtained by dehydration-condensation of 2 to 10 monosaccharides and having at least one α-1,4 linkage. An oligosaccharide has preferably 3 to 9 saccharide units, more preferably 4 to 8 saccharide units, and even more preferably 5 to 7 saccharide units. Examples of the oligosaccharide having an α-1,4 linkage include malto-oligosaccharides, such as maltose, maltotriose, maltotetraose, maltopentaose, maltohexaose, maltoheptaose, malto-octaose, maltononaose, and maltodecaose. An oligosaccharide may be a straight-chain oligosaccharide or a branched-chain oligosaccharide. An oligosaccharide may have an intramolecular ring structure.

Polysaccharides as used herein refer to compounds generated by dehydration-condensation of at least 11 monosaccharides and having at least one α-1,4 linkage. Examples of polysaccharides include dextrin, amylose, amylopectin, and starch. A preferable polysaccharide is dextrin.

Dextrins refer to substances obtained by lowering the molecular weight of starch by a chemical or enzymatic method. Examples of dextrins include British gum, yellow dextrin, white dextrin, PINE-DEX (Matsutani Chemical Industry Co., Ltd.), SUNDECK (Sanwa Cornstarch Co., Ltd.), and Tetrup (Hayashibara Shoji Co., Ltd.).

Amylose is a straight-chain molecule composed of glucose units linked together by α-1,4 linkages. Amylose is contained in natural starch.

Amylopectin is a branched-chain molecule composed of glucose units linked together by α-1,4 linkages to which glucose units are linked together by α-1,6 linkages. Amylopectin is contained in natural starch. As amylopectin, for example, waxy corn starch consisting of 100% amylopectin may be used.

Starch is a mixture of amylose and amylopectin. As starch, any starch which is usually commercially available may be used. The ratio of amylose to amylopectin contained in starch varies depending on the type of plant which produces the starch. The majority of starch contained in waxy rice, waxy corn, and the like is amylopectin. Starch is divided into natural starch, starch degradation products, and processed starch.

Natural starch is divided into tuber starch and cereal starch according to the raw material from which it is derived. Examples of tuber starch include potato starch, tapioca starch, sweet potato starch, kudzu starch, bracken starch, and the like. Examples of cereal starch include corn starch, wheat starch, rice starch, and the like.

Processed starch is starch obtained by subjecting natural starch to treatment, such as hydrolysis, esterification, gelatinization, or the like, to confer properties for better ease of utilization. A wide variety of processed starches are available which have various combinations of properties, such as, for example, temperature at which gelatinization starts, the viscosity of the starch paste, the transparency of the starch paste, aging stability, and the like. There are various types of processed starch. An example of such starch is starch which is obtained by immersing starch granules in acid at a temperature of no more than the gelatinization temperature of the starch so that starch molecules are cleaved but starch granules are not broken.

Starch degradation products are oligomers or polymers obtained by subjecting starch to treatment, such as enzyme treatment, hydrolysis, or the like, which have a lower molecular weight than before the treatment. Examples of the starch degradation products include starch degraded by a debranching enzyme and starch partially degraded by hydrolysis.

Starch degraded by a debranching enzyme is obtained by allowing a debranching enzyme to act on starch. By changing the action time of the debranching enzyme to various extents, starch degraded by a debranching enzyme in which branching portions (i.e., α-1,6-glucoside linkage) are cleaved to any extent can be obtained.

Starch partially degraded by hydrolysis refers to degradation products obtained by decomposing starch partially by the action of an acid, such as hydrochloric acid, acetic acid, oxalic acid, sulfuric acid, nitric acid, or the like. For starch partially degraded by hydrolysis, the distribution of the molecular weight of the resultant degradation products may vary depending on the type of starch to be degraded. The starch partially degraded by hydrolysis may be a mixture of saccharide chains having various lengths.

(2) Phenol Derivative:

As used herein, "phenol derivative" refers to a compound having a phenol backbone (i.e., a benzene ring) or a flavonoid backbone and having a hydroxyl group linked to the phenol backbone or the flavonoid backbone, including phenol and kojic acid. Examples of the phenol derivative include a compound having a phenolic hydroxyl group on a single phenol or flavonoid backbone, and a compound having at least two phenolic hydroxyl groups on a single phenol or flavonoid backbone. Hereinafter, for the sake of convenience, compounds having one phenolic hydroxyl group on a single phenol or flavonoid backbone are called monophenol type compounds, and compounds having at least two phenolic hydroxyl groups on a single phenol or flavonoid backbone are called polyphenol type compounds.

Compounds having two phenolic hydroxyl groups on a single phenol or flavonoid backbone are called diphenol type compounds.

A phenol derivative glycoside having a phenolic hydroxyl group is also included as a phenol derivative.

Examples of monophenol type compounds having one phenolic hydroxyl group on a single phenol or flavonoid backbone include phenol, kojic acid, dimethoxy phenol, acetaminophen, vanillin, and daidzein.

Examples of monophenol type compounds also include monophenol type flavonoid type compounds. Examples of monophenol type flavonoid type compounds include monophenol type flavone type compounds, monophenol type isoflavone type compounds, monophenol type flavonol type compounds, monophenol type flavanone type compounds, monophenol type flavanonol type compounds, monophenol type catechin type compounds, monophenol type aurone type compounds, monophenol type chalcone type compounds, and monophenol type dihydrochalcone type compounds.

Examples of dimethoxy phenols include 2,3-dimethoxy phenol, 2,4-dimethoxy phenol, 2,5-dimethoxy phenol, 2,6-dimethoxy phenol, 3,4-dimethoxy phenol, and 3,5-dimethoxy phenol. 3,4-dimethoxy phenol and 3,5-dimethoxy phenol are preferable.

Examples of polyphenol type compounds having at least two phenolic hydroxyl groups on a single phenol or flavonoid backbone include hydroquinone, epigallocatechin, epicatechin gallate, anthocyanidin type compounds, anthocyanin type compounds, caffeic acid, catechol, resorcinol, protocatechuic acid, gallic acid, genistein, β-resorcylic acid, and phloroglucinol.

Examples of diphenol compounds also include diphenol type flavonoid type compounds. Examples of diphenol type flavonoid type compounds include diphenol type flavone type compounds, diphenol type isoflavone type compounds, diphenol type flavonol type compounds, diphenol type flavanone type compounds, diphenol type flavanonol type compounds, diphenol type catechin type compounds, diphenol type aurone type compounds, diphenol type chalcone type compounds, and diphenol type dihydrochalcone type compounds.

Examples of resorcylic acids include α-resorcylic acid, β-resorcylic acid, and γ-resorcylic acid. In the present invention, β-resorcylic acid is preferable.

Hydroquinone, catechin-type compounds, epigallocatechin, epicatechin gallate, 3,4-dimethoxy phenol, 3,5-dimethoxy phenol, and acetaminophen are preferable for the method of the present invention. Hydroquinone is more preferable.

A phenol derivative may be isolated from a natural product, or obtained by modifying a natural compound (i.e., semi-synthesis), or newly synthesized. The more complicated the structure of a phenol derivative, extraction from a natural product or semi-synthesis becomes more preferable.

Methods of isolating a phenol derivative, methods of semi-synthesizing a phenol derivative, and methods of synthesizing a phenol derivative are known in the art, and can be conducted in accordance with known techniques.

(3) Enzyme:

An enzyme used in the method of the present invention is selected from the group consisting of neopullulanase, cyclomaltodextrinase, maltogenic α-amylase, and saccharifying amylase having cyclodextrin synthesizing capability.

The enzyme used in the present invention is not necessarily a purified enzyme, if an activity to glycosylate a phenol derivative can be detected in the enzyme. Even an unpurified bacterial culture or a crude enzyme partway through a purification step may be used in the production method of the present invention. The above-described enzymes may be produced from bacterial culture in accordance with a method known in the art, or maybe commercially available enzymes.

Neopullulanase refers to an enzyme which mainly hydrolyzes an α-1,4-glucoside linkage of pullulan, and which has ability to produce mainly panose. Furthermore, the enzyme may carry out a glycosyl transfer reaction.

Example of neopullulanases include neopullulanases derived from a *bacterium* selected from the group consisting of *Thermoactinomyces vulgaris, Bacteroides thetaiotaomicron, Pseudomonas, Bacillus polymyxa, Bacillus licheniformis, Bacillus stearothermophilus, Bacillus thermoamyloliquefaciens,* and *Thermus thermophilus*.

Examples of particularly preferable neopullulanase include neopullulanase derived from *Bacillus stearothermophilus* TRS40 (Deposit No. FERM P-9609) (Journal of Bacteriology, Vol. 170, p. 1554, 1988), α-amylase derived from *Thermoactinomyces vulgaris* (Agricultural and Biological Chemistry, Vol. 42, p. 1681, 1978), and neopullulanase type α-amylase derived from *Thermoactinomyces vulgaris* (Biosci. Biotechnol. Biochem., Vol. 57, p. 395, 1993), a pullulan hydrolase of *Bacillus stearothermophilus* KP1064 (Applied Microbiology and Biotechnology, Vol. 21, p. 20, 1985), neopullulanase of *Bacteroides thetaiotaomicron* 95-1 (Journal of Bacteriology, Vol. 173, p. 2926, 1991), neopullulanase derived from *Bacillus polymyxa* (Applied Biochemistry and Biotechnology, Vol. 68, p. 113, 1997), amylase derived from *Bacillus licheniformis* (J. Biol. Chem., Vol. 267, p. 22108, 1992), neopullulanase derived from Bacillus sp. KSM-1876 (Biosci. Biotechnol. Biochem., Vol. 56, p. 514, 1992), and the like.

Neopullulanase is characterized in that its reactivity with amylose is significantly higher than its reactivity with amylopectin. When neopullulanase is allowed to react with starch, amylose in the starch is degraded mainly into maltose. It is believed that the hydrolysis of amylopectin by neopullulanase is inhibited in the presence of a saccharide having a polymerization degree greater than or equal to that of a disaccharide, such as maltose, and the inhibition eventually further leads to the higher reactivity with amylose than the reactivity with amylopectin. Neopullulanase does not necessarily entirely lack action on amylopectin, but may degrade amylopectin to some extent to reduce the molecular weight of the amylopectine. Therefore, even if starch consisting mostly or substantially entirely of amylopectin is a substrate, neopullulanase may produce its particular product having reduced molecular weight.

Neopullulanase may be prepared in accordance with a known method, for example, Japanese Patent No. 1853673 or No. 1985401.

Cyclomaltodextrinase refers to an enzyme which degrades malto-oligosaccharides having a polymerization degree greater than or equal to that of maltotriose and cyclodextrins, and hardly degrades amylopectin, glycogen, panose, and isopanose. Cyclomaltodextrinase is described in Japanese Laid-Open Publication No. 5-68486. In Japanese Laid-Open Publication No. 7-289280, cyclomaltodextrinase is defined as having a substrate specificity in hydrolysis rate or affinity to cyclodextrin greater than that of polysaccharides or straight-chain oligosaccharide having the same polymerization degree as that of cyclodextrin. Appl. Microbiol. Biotechnol. 39:197–203(1993) describes that cyclomaltodextrinase hydrolyzes cyclodextrin (CD) more rapidly than starch and amylopectin; cyclomaltodextrinase does not produce CD from starch and therefore is different from CGTase: and cyclomaltodextrinase is similar to neopullulanase in terms of the primary structure of the amino acid sequence.

Examples of cyclomaltodextrinase include cyclomaltodextrinases derived from a *bacterium* selected from the group consisting of *Bacillus stearothermophilus, Bacillus thermophilus* (*Thermus thermophilus*), *Bacillus coagulanc, Escherichia coli, Flavobacterium, Alkalophillic Bacillus,* and *Bacillus sphaericus*.

Examples of preferable cyclomaltodextrinase include cyclomaltodextrinases derived from *Bacillus sphaericus* (Appl. Microbiol. Biotechnol. 39:197–203(1993): hereinafter referred to as BSCDase) and cyclomaltodextrinase derived from *Alkalophilic Bacillus* sp. A2-5a strain (deposition number: FERM-P-13846, Bioscience Biotech. Biochem., 58(3), 517–520(1994): hereinafter referred to as A2-5a CDase).

Maltogenic α-amylase refers to an enzyme which acts on glucan in an endo type reaction to produce α-anomer maltose. J. Biol. Chem. 267(31) 22108–22114, 1992 describes that maltogenic α-amylase cleaves an α-1,4-glucoside linkage (provided that it cannot cleave the α-1,4-glucoside linkage subsequent to an α-1,6-glucoside linkage); maltogenic α-amylase has transfer activity; maltogenic α-amylase degrades cyclodextrin; and maltogenic α-amylase is similar to neopullulanase in terms of the primary structure of the amino acid sequence.

Examples of maltogenic α-amylase include maltogenic α-amylases derived from a *bacterium* selected from the group consisting of *Thermoactinomyces vulgaris, Bacteroides thetaiotaomicron, Pseudomonas, Bacillus polymyxa, Bacillus licheniformis, Bacillus stearothermophilus, Bacillus thermoamyloliquefaciens, Thermus thermophilus,* and *Bacillus*.

A preferable maltogenic α-amylase is *Bacillus licheniformis*-derived maltogenic α-amylase (referred to as BLMA).

Neopullulanase, cyclomaltodextrinase, and maltogenic α-amylase are all included in the α-amylase family. The α-amylase family is defined by the similarity in structure and catalyst mechanism of enzymes included in the family. Specifically, the α-amylase family is defined as having the following properties.

The members of the family
1. act on an α-glucoside linkage;
2. hydrolyze an α-glucoside linkage to produce α-anomer glucose or malto-oligosaccharide, or catalyze a glycosyl transfer reaction to form a new α-glucoside;
3. have four conservative regions on the primary structure, which are common to each enzyme, where all catalyzing sites and most substrate binding sites are present in the conservative regions; and
4. have Asp, Glu and Asp residues corresponding to Asp206, Glu230 and Asp297 of Takaamylase A as a catalytic site.

As described above, an enzyme included in the α-amylase family is known to have four regions having high homology, i.e., conservative regions, as a result of comparison of the primary structures of the amino acid sequences. As used herein, the conservative region of the α-amylase-family enzyme refers to Regions 1, 2, 3 and 4 shown in FIG. 1 in Journal of Bioscience and Bioenginieering, Vol. 87, pp. 557–565 (1999) (referred to as conservative regions 1, 2, 3 and 4). The conservative regions 1 to 4 are present in an A domain having a structure containing 8 repeats of a β strand and a α helix (referred to as $(\beta/\alpha)_8$-barrel structure). In some enzymes of the α-amylase family, conservative region 1 begins with about amino acid position 120 from the N terminus (e.g., α-amylase (originating from *Aspergillus oryzae*)). However, the α-amylase family also includes some enzymes whose conservative region 1 begins with amino acid position about 240 from the N terminus (preferably, an amino acid position from 239 to 242). The numbering of amino acids in the above-described enzymes begins with the N terminus of the mature form. Neopullulanase, cyclomaltodextrinase and maltogenic α-amylase used in the present invention may have the characteristic of the latter amino acid sequence. Such an enzyme may also have another domain (N domain) composed of at least 100 amino acids before A domain.

Neopullulanase, cyclomaltodextrinase and maltogenic α-amylase used in the present invention contain an amino acid sequence which contains conservative regions 1, 2, 3 and 4 of the α-amylase family enzyme from the N terminus in this order. In neopullulanase, cyclomaltodextrinase and maltogenic α-amylase used in the present invention, conservative region 1 in the α-amylase family enzyme may begin with an amino acid position from 239 to 242 from the N terminus or a position substantially equivalent to those positions. A "position substantially equivalent to" may be a position located 1 to 10 amino acids, preferably 1 to 5 amino acids, more preferably 1 to 3 amino acids, even more preferably 1 to 2 amino acids, and still more preferably 1 amino acid away from the represented positions (i.e., amino acid positions from 239 to 242) toward the N or C terminus. Most preferably, in the amylose-specific enzyme, conservative region 1 begins with positions from 239 to 242 from the N terminus.

A saccharifying amylase having cyclodextrin synthesizing capability refers to α-amylase which synthesizes cyclodextrin having a polymerization degree of at least 6 at the initial stage of a reaction, and eventually produces glucose, maltose and maltotriose.

Examples of saccharifying amylases having cyclodextrin synthesizing capability is saccharifying amylases having cyclodextrin synthesizing capability derived from a bacteria selected from the group consisting of *Bacillus subtilis* represented by strain IFO14140, *Streptococcus bovis*, *Streptomyces hygroscopicus*, *Streptomyces praecox*, *Rhizopus delemar*, and *Aspergillus niger*.

Examples of *Bacillus subtilis* strains producing saccharifying amylase having cyclodextrin synthesizing capability, include strain IFO14140 (available from Institute For Fermentation, Osaka, Japan (abbreviated as IFO)), *Bacillus* strain 1A289 from Ohio University, *Bacillus* Genetic Stock Center, and strains K02, K05, K12 and D11 described in Okada et al., "Journal of Fermentation Technology Vol. 41, No. 8, 427(1963)". It is first herein disclosed that strains K02, K05, K12 and D11 described in Okada et al. synthesize saccharifying amylase having cyclodextrin synthesizing capability. Okada et al. describes sources from which bacteria producing saccharifying α-amylase were obtained, a screening method for the bacteria, and a method of measuring α-amylase activity. According to Okada et al., primary screening can be performed to obtain bacteria strains producing saccharifying amylase. The obtained bacteria strains producing saccharifying amylase can be subjected to second screening in accordance with a method described in Nishimura et al., J. Ferment. Bioeng., 71, 26(1996), thereby selecting bacteria strains producing an enzyme having cyclodextrin synthesizing capability. A saccharifying amylase having cyclodextrin synthesizing capability produced by *Bacillus subtilis* is described in J. Ferment. Bioeng., 81, 26(1996).

Among bacteria such as *Streptococcus bovis*, *Streptomyces hygroscopicus*, *Streptomyces praecox*, *Rhizopus delemar*, and *Aspergillus niger*, a *bacterium* producing saccharifying amylase is highly likely to produce saccharifying amylase having cyclodextrin synthesizing capability. Therefore, bacteria producing saccharifying amylase may also be preferably used. Whether or not the bacterium producing saccharifying amylase produces saccharifying amylase having cyclodextrin synthesizing capability may be confirmed by a method described in Nishimura et al., J. Ferment. Bioeng., 81, 26(1996).

Saccharifying amylase having cyclodextrin synthesizing capability hydrolyzes a wide variety of saccharide substrates to transfer glucose onto various phenol derivatives, thereby obtaining various phenol derivative glycosides.

Saccharifying amylase having cyclodextrin synthesizing capability may be prepared based on a known method, for example, a method described in Okada et al., "Journal of Fermentation Technology Vol. 41, No. 8, 427(1963)".

Neopullulanase, cyclomaltodextrinase, maltogenic α-amylase and saccharifying amylase having cyclodextrin synthesizing capability used in the present invention may be produced by a microorganism into which a gene coding for the enzyme is introduced by a genetic recombination method. For example, as to neopullulanase, the base sequence of neopullulanase derived from *Bacillus stearothermophilus* (J. Gen. Microbiol., Vol. 135, p. 1521 (1989)) and the amino acid sequence thereof (Japanese Laid-Open Publication No. 7-177891; procedures for recombination are also described) may be utilized. Alternatively, by searching a DNA library from a plant, a microorganism, or the like using a primer designed based on a known sequence, new neopullulanase, cyclomaltodextrinase, maltogenic α-amylase or saccharifying amylase having cyclodextrin synthesizing capability may be obtained. Utilization of such new enzymes also falls within the scope of the present invention.

A polypeptide enzyme, such as Neopullulanase, cyclomaltodextrinase, maltogenic α-amylase and saccharifying amylase having cyclodextrin synthesizing capability used in the present invention, having 1 to about 10 amino acid residue additions, 1 to about 10 amino acid residue deletions, or 1 to about 10 amino acid residue substitutions may exhibit a desirable biological activity, such as amylose specificity. About 10 to several to 1 amino acid residue additions, deletions or substitutions may be included in the above-described polypeptide enzyme. Preferably, 10, 8, 5, 3, 2 or 1 amino acid residue additions, deletions or substitutions may be included in the above-described polypeptide enzyme. Preferably, such amino acid residue deletions, additions or substitutions are present in anon-conservative region of the α-amylase family. When a substitution is performed, the substitution is preferably a conservative substitution. Conservative substitutions are well known to those skilled in the art.

Those skilled in the art can easily obtain such an enzyme from nature by screening. Moreover, such a polypeptide may be prepared by a genetic engineering technique known to those skilled in the art.

Enzymes used in the present invention maybe prepared in the following manner, for example. Initially, a bacterium producing an enzyme used in the present invention is cultured. This *bacterium* may be a *bacterium* which directly produces the enzyme. Alternatively, a gene coding the enzyme may be cloned, and a bacterium, which is advantageous for enzyme expression, may be transformed with the resultant gene to obtain a transformed *bacterium* which may be used for carrying out the present invention.

The transformation of the *bacterium* using the cloned gene may be performed by a method well known to those skilled in the art. When the cloned gene is used, it is preferable that the gene is operatively linked to a constitutive or inducible promoter. "Operatively linked" indicates that a promoter is linked to a gene in such a manner that the promoter can regulate the expression of the gene. When an inducible promoter is used, culture is preferably performed under inducible conditions. Various inducible promoters are known to those skilled in the art.

A signal peptide may be linked to the cloned gene so that a produced enzyme can be secreted outside the bacterium. Signal peptides are known to those skilled in the art.

Those skilled in the art may set appropriate conditions for culturing bacteria for the purposes of production of an enzyme. Appropriate media for bacterial culture, appropriate conditions for induction of each inducible promoter, and the like are known to those skilled in the art.

The enzyme is recovered from culture after culturing for an appropriate time. When a produced enzyme is secreted outside bacteria, the bacteria are removed by centrifugation to obtain a supernatant. When the produced enzyme is not secreted, the bacteria are destroyed by sonication, mechanical destruction, chemical destruction, or the like to obtain a cell homogenate. Thereafter, the cell homogenate is centrifuged to remove cell debris, thereby obtaining a supernatant. From the resultant supernatant, the enzyme of the present invention maybe recovered by a well-known method, including ammonium sulfate precipitation or ethanol precipitation, acid extraction, anion or cation exchange chromatography, phosphocellulose chromatography, hydrophobic interaction chromatography, affinity chromatography, hydroxyl apatite chromatography, and lectin chromatography. The recovered product may be optionally purified.

The enzyme used in the present invention may be either a purified enzyme or a crude enzyme, and may be either immobilized or not immobilized. The reaction may be either a batch reaction or continuous reaction. As a method for the immobilization, a carrier binding method (e.g., a covalent binding method, an ionic binding method, or a physical adsorption method), a cross-linking method, an entrapment method (lattice type or microcapsule type), or the like, which are well known to those skilled in the art, may be used.

(Method of Measuring Enzyme Activity)

The activity of an enzyme is measured in the following manner.

200 μl of 1.5% w/w soluble starch aqueous solution (the soluble starch is manufactured by Merck; and adjusted with 40 mM acetic acid-Na buffer solution to pH 5.5) incubated at 40° C. is added to 50 μl of enzyme solution incubated at 40° C. and is allowed to react at 40° C. for 10 minutes. To the reaction product, 2 ml of solution in which 0.5N acetic acid and 0.5N hydrochloric acid are mixed at a ratio of 5:1 is added, and the obtained mixture is stirred, thereby stopping the reaction. 0.1 ml of the resultant solution is collected, to which 5 ml of solution containing 0.005% iodine and 0.05% potassium iodide is added, and the resultant mixture is stirred. The mixture is allowed to stand at room temperature for 20 minutes, thereby developing color by the iodine-starch reaction. Thereafter, the absorbance of the solution is measured at 660 nm. The resultant absorbance is represented by C. Apart from this, a solution is prepared as a blank using purified water instead of the above-described enzyme solution, which is subjected to the same procedures to measure its absorbance. The resultant absorbance is represented by B. Based on the thus-obtained C and B, the activity of the enzyme (represented by A) is obtained according to the following formula:

$A=(B-C)/B \times 10$ where one unit of the enzyme activity is 10% of value B.

(Method of Measuring Glycosyl Transfer Rate)

A glycosyl transfer rate is measured as follows.

A solution containing a donor, such as soluble starch or maltopentaose, and an acceptor, such as hydroquinone or catechin, and an enzyme solution are mixed together and allowed to react at 40° C. for 16 to 24 hours. The reaction product is analyzed by HPLC (a ODS column RP-18 manufactured by Merck; and 10% methanol eluent adjusted to pH 2.5 is used). The absorbance of HPLC fractions are measured at 280 nm to detect and quantify the glycoside. The peak area of the glycoside is obtained. As a control, a solution is prepared using purified water instead of an enzyme solution, and the same procedures as described above are performed to measure the amount of the acceptor. The peak area of the acceptor is obtained.

A glycosyl transfer rate is calculated by the following formula:

Glycosyl transfer rate=the peak area of glycoside/the peak area of a control acceptor×100

(Reaction of Phenol Derivative with Saccharide)

In the method of producing a phenol derivative glycoside according to the present invention, any reaction conditions, such as pH and temperature, may be used, as long as the phenol derivative glycoside can be produced, in a step of allowing the above-described saccharide and the above-described phenol derivative to react with each other in the presence of an enzyme. The concentrations of the saccharide and the phenol derivative may be determined by considering reaction conditions and the like. At the start of the enzyme reaction, the total amounts of the glycosyl donor (e.g., dextrin) and the phenol derivative do not need to be dissolved in a reaction system solvent. Even if only a very small amount of dextrin is dissolved, the reaction can start. For example, even if a portion of the dextrin is not dissolved, some dissolved dextrin allows a reaction to start. As the enzyme reaction proceeds, the undissolved dextrin is gradually dissolved, which causes the reaction to further proceed. Similarly, even if a portion of the phenol derivative is not dissolved, as the enzyme reaction proceeds, undissolved phenol derivative is gradually dissolved, which causes the reaction to further proceed.

When the enzyme is neopullulanase, the pH of the reaction system is preferably about 4.0 to about 8.0, and in terms of the reaction rate, the efficiency, the enzyme stability, and the like, more preferably about 5.0 to about 7.5, and more preferably about 5.5 to about 7.0. The temperature is preferably about 10° C. to about 80° C., and in terms of the reaction rate, the efficiency, the enzyme stability, and the like, more preferably about 20° C. to about 60° C., and more preferably about 40° C. The reaction time is preferably about 1 to 100 hours, more preferably about 1 to 50 hours, and even more preferably about 16 hours. The phenol derivative concentration is preferably about 0.1% by weight to about 50% by weight, and in terms of the reaction rate, the efficiency, the ease of handling a substrate solution, and the like, more preferably about 1% by weight to about 20% by weight, and even more preferably about 1% by weight to about 5% by weight. The saccharide concentration is preferably about 0.1% by weight to about 70% by weight, and in terms of the reaction rate, the efficiency, the ease of handling a substrate solution, and the like, more preferably about 1% by weight to about 20% by weight, and even more preferably about 5% by weight to about 10% by weight. The amount of the enzyme used is determined by a relationship with the reaction time and the substrate concentration. Typically, it is preferable that the enzyme amount is selected such that the reaction is ended in about 1 hour to about 72 hours. It is typically preferable that the amount of the enzyme used is about 50 to 10,000 units per 1 g of the substrate.

When the enzyme is cyclomaltodextrinase, the pH of the reaction system is preferably about 4.0 to about 8.0, and in terms of the reaction rate, the efficiency, the enzyme stability, and the like, more preferably about 5.0 to about 7.5, and even more preferably about 6.0 to about 7.0. The temperature is preferably about 10° C. to about 80° C., and in terms of the reaction rate, the efficiency, the enzyme stability, and the like, more preferably about 20° C. to about 60° C., and even more preferably about 40° C. The reaction time is preferably about 1 to 100 hours, more preferably about 1 to 50 hours, and even more preferably about 16 hours. The phenol derivative concentration is preferably about 0.1% by weight to about 50% by weight, and in terms of the reaction rate, the efficiency, the ease of handling a substrate solution, and the like, more preferably about 1% by weight to about 20% by weight, and even more preferably about 1% by weight to about 5% by weight. The saccharide concentration is preferably about 0.1% by weight to about 70% by weight, and in terms of the reaction rate, the efficiency, the ease of handling a substrate solution, and the like, more preferably about 1% by weight to about 20% by weight, and even more preferably about 5% by weight to about 10% by weight. The amount of the enzyme used is determined by a relationship with the reaction time and the substrate concentration. Typically, it is preferable that the enzyme amount is selected such that the reaction is ended in about 1 hour to about 72 hours. It is typically preferable that the amount of the enzyme used is about 50 to 10,000 units per 1 g of the substrate.

When the enzyme is maltogenic α-amylase, the pH of the reaction system is preferably about 4.0 to about 8.0, and in terms of the reaction rate, the efficiency, the enzyme stability, and the like, more preferably about 5.0 to about 7.5, and even more preferably about 5.5 to about 7.0. The temperature is preferably about 10° C. to about 80° C., and in terms of the reaction rate, the efficiency, the enzyme stability, and the like, more preferably about 20° C. to about 60° C., and even more preferably about 40° C. The reaction time is preferably about 1 to 100 hours, more preferably about 1 to 50 hours, and even more preferably about 16 hours. The phenol derivative concentration is preferably about 0.1% by weight to about 50% by weight, and in terms of the reaction rate, the efficiency, the ease of handling a substrate solution, and the like, more preferably about 1% by weight to about 20% by weight, and even more preferably about 1% by weight to about 5% by weight. The saccharide concentration is preferably about 0.1% by weight to about 70% by weight, and in terms of the reaction rate, the efficiency, the ease of handling a substrate solution, and the like, more preferably about 1% by weight to about 20% by weight, and even more preferably about 5% by weight to about 10% by weight. The amount of the enzyme used is determined by a relationship with the reaction time and the substrate concentration. Typically, it is preferable that the enzyme amount is selected such that the reaction is ended in about 1 hour to about 72 hours. It is typically preferable that the amount of the enzyme used is about 50 to 10,000 units per 1 g of the substrate.

When the enzyme is saccharifying amylase having cyclodextrin synthesizing capability, the pH of the reaction system is typically about 3.0 to about 11.0, and in terms of the reaction rate, the efficiency, the enzyme stability, and the like, preferably about 4.0 to about 7.0, and more preferably about 4.0 to about 6.5. The reaction temperature is about 10° C. to about 80° C., and in terms of the reaction rate, the efficiency, the enzyme stability, and the like, preferably about 30° C. to about 60° C. The reaction time is typically about 3 to 72 hours, preferably about 10 to 24 hours, and more preferably about 16 hours. The phenol derivative concentration is typically about 1% by weight to about 40% by weight, and in terms of the reaction rate, the efficiency, the ease of handling a substrate solution, and the like, preferably about 1% by weight to about 40% by weight, and more preferably about 5% by weight to about 20% by weight. The saccharide concentration is typically about 1% by weight to about 50% by weight, and in terms of the reaction rate, the efficiency, the ease of handling a substrate solution, and the like, and preferably about 10% by weight to about 50% by weight. The amount of the enzyme used is determined by a relationship with the reaction time and the substrate concentration. Typically, it is preferable that the enzyme amount is selected such that the reaction is ended in about 10 hour to about 24 hours. It is typically preferable that the amount of the enzyme used is about 10 to 10,000 units per 1 g of the substrate.

(Isolation and Purification of Product)

The phenol derivative glycoside obtained by the above-described reaction may be isolated and purified by an isolation method well known to those skilled in the art. For example, the purification is achieved by using partition using various solvents (e.g., methanol and ethanol) and chromatography (e.g., gel filtration chromatography and HPLC) alone or in combination.

The phenol derivative glycoside obtained by the above-described reaction is preferably purified by chromatography using an ion exchange resin. The ion exchange resin maybe either a cation exchange resin or an anion exchange resin. A cation exchange resin is more preferable. This is because the interaction between the cation exchange resin or a metal (e.g., calcium, lead, zinc, and sodium) or hydrogen bound to the anion exchange resin, and the phenol derivative, or the interaction between a portion or whole of the anion exchange resin and the phenol derivative glycoside, is changed by glycosylation of the phenol derivative. The interaction between the portion or whole of the anion exchange resin and the phenol derivative glycoside is inferred to probably be based on the hydrophobic interaction between the entirety of the resin and the phenol derivative glycoside. If chromatography using a cation exchange resin or an anion exchange resin is used for purification, glycoside can be purified by a single step.

Any cation exchange resin may be used as long as it can separate the phenol derivative from the phenol derivative glycoside. Examples of the cation exchange resin include commercially available DIAION SK1B, DIAION SK104, DIAION SK110, DIAION PK208, DIAION PK212, DIAION PK216, DIAION UBK530, and DIAION UBK550 (manufactured by Mitsubishi Chemical Corporation); and CR-1310, CR-1320, Amberlite IR120B, Amberlite 200CT, and IRC50 (manufactured by Organo Corporation).

Any anion exchange resin may be used as long as it can separate the phenol derivative from the phenol derivative glycoside. Examples of the anion exchange resin include commercially available PA412, WA-30 and PA-308 (manufactured by Mitsubishi Chemical Corporation); as well as IRA96SB, IRA910CT, XT6050RF and IRA900 (manufactured by Organo Corporation). It is preferable to use a styrene-based anion exchange resin which is, for example, pretreated to convert it into Cl type, acetic acid type, carbonic acid type, or nitric acid type in order to suppress anion exchange. More preferably, the anion exchange resin is a styrene-based anion exchange resin which is pretreated to convert it into the Cl type.

By chromatography using a cation exchange resin or an anion exchange resin, a phenol derivative glycoside, a saccharide as a byproduct (e.g., isomalto-oligosaccharide), and an unreacted phenol derivative can be recovered in respective separate fractions. Therefore, these fractionated substances can be effectively reused.

In the method of the present invention, simulated moving bed column chromatography which can continuously perform purification can be optionally performed.

(Use of Phenol Derivative Glycoside)

Phenol derivative glycosides obtained by the method of the present invention may be used as a substitute for a phenol derivative in various uses. In particular, these phenol derivative glycosides may be used in food and drink compositions, food additive compositions, infusions, adhesive compositions, antiaging agents for starch, oral compositions, drugs, quasi-drugs, and cosmetics. In these uses, the phenol derivative glycosides may be used in concentrations appropriate for individual uses.

EXAMPLES

Production Example 1

Preparation of Cyclomaltodextrinase

The chromosome of *Alkalophilic Bacillus* sp. strain A2-5a (deposition number: FERM-P-13864) was prepared by a commonly used method. Based on the published base sequence of the cyclomaltodextrinase gene of *Alkalophilic Bacillus* sp. strain A2-5a (DBJ/EMBL/GenBank; AB015670), oligonucleotides having the following sequences were synthesized by a commonly used method, and were used as PCR primers. The sequences of the PCR primers are as follows:

NP6N-NCO: TGGCCATGGTAAAAGAAGCGATTTA (SEQ ID NO: 1); and

NP6N-KPN: TTCGGTACCTTAAATCACCTTTATAACACC (SEQ ID NO: 2).

The prepared chromosome and primers were used to perform PCR (94° C. for 1 minute, followed by 30 cycles of 94° C. for 0.5 minute, 50° C. for 1 minute, and 72° C. for 2 minutes). Thereby, fragments of the cyclomaltodextrinase gene were amplified.

The amplified gene fragment was cleaved with restriction enzymes NcoI and KpnI, and the resultant fragments were ligated with vector pKK388-1 (manufactured by Clontech) which had been previously cleaved with the same enzymes, thereby obtaining recombinant plasmid pNPR63. This plasmid was introduced into *E. coli* strain TG-1 (manufactured by Amersham Pharmacia Biotech) by a commonly used method. Thus, recombinant TG-1 having *Alkalophilic Bacillus* sp. strain A2-5a's cyclomaltodextrinase gene was obtained.

0.01 g of the resultant recombinant strain TG-1 was mixed with 10 ml of L medium (1.0% tryptone, 0.5% yeast extract and 0.5% NaCl) containing 50 μg/ml ampicillin, followed by culturing while shaking at 37° C. overnight, thereby obtaining a preculture.

10 ml of this preculture was added to a 2-liter Sakaguchi flask containing 1 liter of Terrific medium (manufactured by Life Technologies Oriental, Inc.), containing 50 μg/ml ampicillin. The flask was shaken by an incubator shaker at 37° C. for 3 hours. Thereafter, the set temperature of the incubator shaker was changed to 15° C. and the flask was shaken at 15° C. for 30 minutes. Thereafter, isopropyl-β-D-galactopyranoside (IPGP, manufactured by Wako Pure Chemical Industries, Ltd.) was added to the flask to a final concentration of 0.1 mM, followed by further shaking at 15° C. for 20 hours.

Thereafter, the resultant product was centrifuged at 10,000 rpm for 10 minutes, and the bacteria were recovered. The obtained bacteria were suspended in 50 ml of 10 mM sodium phosphate buffer solution (pH 7.5) (hereinafter referred to as buffer solution ML). The suspension was subjected to sonication, thereby destroying the bacteria. Thereafter, the product was centrifuged at 10,000 rpm for 10 minutes to remove insoluble cell debris, thereby obtaining a crude enzyme solution.

Ammonium sulfate was added to the crude enzyme solution to a concentration of 70% saturation, thereby precipitating cyclomaltodextrinase. The cyclomaltodextrinase precipitate was suspended in about 20 ml of buffer solution ML. Thereafter, the suspension was dialyzed against buffer solution ML, changing the buffer solution once a day for 3 days.

After dialysis, the suspension was loaded onto a Q-Sepharose column (manufactured by Amersham Pharmacia Biotech) equilibrated with buffer solution ML. This column was washed with buffer solution ML containing 0.2 M NaCl, followed by flowing buffer solution ML containing 0.4 M NaCl, thereby eluting cyclomaltodextrinase.

The resultant active fraction was dialyzed against buffer solution ML, changing the buffer solution once a day for 3 days. After the dialysis, the solution was loaded to a Resource Q column (manufactured by Amersham Pharmacia Biotech) equilibrated with buffer solution ML. This column was washed with buffer solution ML containing 0.2M NaCl. Thereafter, cyclomaltodextrinase was eluted by linearly increasing the NaCl concentration of the buffer solution ML up to 0.4 M. The resultant active fraction was dialyzed against buffer solution ML, changing the buffer solution once a day for 3 days, thereby obtaining a purified cyclomaltodextrinase solution.

Production Example 2

Preparation of Maltogenic α-Amylase

The chromosome of *Bacillus licheniformis* strain ATCC27811 was prepared by a commonly used method. Based on the published base sequence of the maltogenic α-amylase gene of *Bacillus licheniformis* strain ATC027811 (also referred to as the BLMA gene) (Kim, I. C. et al., J. Biol. Chem., 267, 11108–22114 (1992)), oligonucleotides having the following sequences were synthesized by a commonly used method, and were used as POR primers. The sequences of the PCR primers are as follows:

NP4N-NDE: TGGCATATGATCGAATTAGCAGCGATAC (SEQ ID NO: 3); and

NP4N-ECO: CTTGAATTCTTAACAGAATTTAGACCGC (SEQ ID NO: 4).

The prepared chromosome and primers were used to perform PCR (94° C. for 1 minute, followed by 30 cycles of 94° C. for 0.5 minute, 50° C. for 1 minute, and 72° C. for 2 minutes). Thereby, fragments of the maltogenic α-amylase gene were amplified.

The amplified gene fragment was cleaved with restriction enzymes NdeI and EcoRI. The resultant fragments were ligated with vector pGEX-Nde2 which had been previously cleaved with the same enzymes, thereby obtaining recombinant plasmid pNPR63. pGEX-Nde2 is a plasmid in which four bases, CTGA, was inserted using DNA polymerase into the unique XbaI restriction enzyme cleavage site of pGEX- Nde described in Terada et al, Applied and Environmental Microbiology, 165:910–915 (1999). This plasmid was introduced into *E. coli* strain TG-1 (manufactured by Amersham Pharmacia Biotech) by a commonly used method. Thus, recombinant strain TG-1 having *Bacillus licheniformis* strain ATCC27811's maltogenic α-amylase gene was obtained.

0.01 g of the recombinant TG-1 was mixed with 10 ml of L medium containing 50 μg/ml ampicillin, followed by culturing while shaking at 37° C. overnight, thereby obtaining a preculture.

10 ml of this preculture was added to a 2-liter Sakaguchi flask containing 1 liter of Terrific medium (manufactured by Life Technologies Oriental, Inc.), containing 50 μg/ml ampicillin. The flask was shaken at 37° C. for 3 hours. Thereafter, the set temperature of the incubator shaker was changed to 15° C. and the flask was shaken at 15° C. for 30 minutes. Thereafter, isopropyl-β-D-galactopyranoside (IPGP, manufactured by Wako Pure Chemical Industries, Ltd.) was added to the flask to a final concentration of 0.1 mM, followed by further shaking at 15° C. for 20 hours.

Thereafter, the product was centrifuged at 10,000 rpm for 10 minutes, and the bacteria were recovered. The obtained bacteria were suspended in 50 ml of 10 mM sodium phosphate buffer solution (pH 7.5) (hereinafter referred to as buffer solution ML). The suspension was subjected to sonication, thereby destroying the bacteria. Thereafter, the product was centrifuged at 10,000 rpm for 15 minutes to remove insoluble cell debris, thereby obtaining a crude enzyme solution.

Ammonium sulfate was added to the crude enzyme solution to a concentration of 70% saturation, thereby precipitating maltogenic α-amylase. The maltogenic α-amylase precipitate was suspended in about 20 ml of buffer solution ML. Thereafter, the suspension was dialyzed against buffer solution ML, changing the buffer solution once a day for 3 days.

After dialysis, the suspension was loaded to a Q-Sepharose column (manufactured by Amersham Pharmacia Biotech) equilibrated with buffer solution ML. This column was washed with buffer solution ML containing 0.4 M NaCl, followed by flowing buffer solution ML containing 1.0 M NaCl, thereby eluting maltogenic α-amylase.

The resultant active fraction was dialyzed against buffer solution ML, changing the buffer solution once a day for 3 days, thereby obtaining a purified maltogenic α-amylase solution.

Example 1

Production of
Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid-Na buffer solution (pH 5.5), thereby obtaining a solution containing 10% by weight hydroquinone and 20% by weight maltopentaose. To 10 ml of this solution, 10 ml of an enzyme solution containing saccharifying amylase having cyclodextrin synthesizing capability with an enzyme activity of 60 units was added, thereby obtaining a mixture. This enzyme solution was prepared using *Bacillus subtilis* strain IFO14140 by a method described in Okada et al. (supra). The mixture was allowed to react at 40° C. for 18 hours. Thereafter, a 3-fold volume of ethyl acetate was added to the reaction product, followed by vigorously shaking the container, thereby arresting the enzyme reaction. Thereafter, the reaction product was allowed to stand at room temperature for 30 minutes, and subsequently an aqueous phase fraction (i.e., the lower layer) was recovered. This procedure was carried out three times, thereby completely removing unreacted hydroquinone. The aqueous phase fraction eventually obtained was vacuum-dried, thereby obtaining a sample.

The sample was dissolved in 10 ml of purified water to obtain a sample solution. This sample solution was applied to an activated charcoal column (manufactured by Wako Pure Chemical Industries, Ltd.) equilibrated with purified water, thereby allowing glycoside to be adsorbed to the activated charcoal column. Thereafter, 200 ml of 20% methanol aqueous solution was used to elute unreacted saccharide adsorbed to the activated charcoal column. Thereafter, 300 ml of 100% methanol was used to elute glycoside. The 100% methanol fraction containing glycoside was vacuum-dried. The residue was dissolved again in purified water, followed by lyophilization. In this manner, about 250 mg of white powder was obtained.

1 mg of this powder and 20 units of α-glucosidase (manufactured by Toyobo) were dissolved in phosphate buffer solution (pH 7.0), thereby obtaining a solution. This solution was incubated at 40° C. for 4 hours. After the incubation, the solution was subjected to HPLC using ODS column RP-18 (manufactured by Merck) where 10% methanol aqueous solution adjusted to pH 2.5 was used as a mobile phase. The absorbance of each fraction of the eluate was measured at 280 nm so as to detect hydroquinone glycoside. As a result, the peak of hydroquinone monoglucoside completely disappeared and a new peak of hydroquinone appeared. Accordingly, it was found that the resultant powder was a glycoside in which glucose was linked to hydroquinone with an α-linkage (hydroquinone monoglucoside).

Further, the structure of the hydroquinone monoglucoside was confirmed with NMR (manufactured by JEOL; JNM-GX270), so that results similar to the above-described results were confirmed.

As a result, it was found that the purity of the resultant hydroquinone monoglucoside was 96%.

Example 2

Production of
Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid—Na buffer solution (pH 5.5), thereby obtaining a solution containing 10% by weight hydroquinone and 40% by weight maltopentaose. To 10 ml of this solution, 10 ml of an enzyme solution containing saccharifying amylase having cyclodextrin synthesizing capability with an enzyme activity of 60 units was added, thereby obtaining a mixture. This enzyme solution had been prepared using *Bacillus subtilis* strain IFO14140 by a method described in Okada et al. (supra). Using a method described in Nishimura et al., J. Ferment. Bioeng., 71, 26(1996), it had been confirmed that the enzyme solution had cyclodextrin synthesizing capability. The mixture was allowed to react at 40° C. for 16 hours.

Thereafter, the reaction product was subjected to gel filtration using Sephadex G-15, thereby obtaining about 800 mg of hydroquinone glycoside (purity 90%).

Example 3

Production of Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid—Na buffer solution (pH 5.5), thereby obtaining a solution containing 5% by weight hydroquinone and 5% by weight maltopentaose. To 10 ml of this solution, 10 ml of an enzyme solution containing neopullulanase with an enzyme activity of 60 units was added, thereby obtaining a mixture. The enzyme solution had been prepared by a method described in Journal of Bacteriology, Vol. 170, p. 1554, 1988 using *Bacillus stearothermophilus* TRS40. This mixture was allowed to react at 40° C. Maltopentaose corresponding to 2% of the weight of the mixture and 30 units of neopullulanase was added to the mixture 3, 8 and 12 hours after the start of the reaction, and the reaction was performed for a total of 24 hours.

Thereafter, the reaction product was subjected to gel filtration using Sephadex G-15, thereby obtaining about 100 mg of hydroquinone glycoside (purity 85%).

In the gel filtration, a fraction different from the one containing hydroquinone glycoside contained saccharides. About 60% of the saccharides contained in this saccharide-containing fraction was isomalto-oligosaccharide.

Example 4

Production of Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid—Na buffer solution (pH 5.5), thereby obtaining a solution containing 5% by weight hydroquinone and 50% by weight maltopentaose. To 10 ml of this solution, 5 ml of an enzyme solution containing cyclomaltodextrinase having an enzyme activity of 10 units was added, thereby obtaining a mixture. The enzyme solution was the *Alkalophilic Bacillus* sp. A2-5a-derived enzyme solution obtained in Production Example 1. The mixture was allowed to react at 40° C. for 16 hours.

Thereafter, the reaction product was subjected to gel filtration using Sephadex G-10, thereby obtaining about 50 mg of hydroquinone glycoside (purity 85%).

In the gel filtration, a fraction different from the one containing hydroquinone glycoside contained saccharides. About 50% of the saccharides contained in this saccharide-containing fraction was isomalto-oligosaccharide.

Example 5

Production of Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid—Na buffer solution (pH 5.5), thereby obtaining a solution containing 3% by weight hydroquinone and 10% by weight maltopentaose. To 10 ml of this solution, 10 ml of maltogenic α-amylase enzyme solution having an enzyme activity of 10 units was added, thereby obtaining a mixture. The enzyme solution was the. *Bacillus licheniformis* ATCC27811 derived enzyme solution obtained in Example 2. Hydroquinone corresponding to 1% of the weight of the reaction mixture, maltopentaose corresponding to 1% of the weight of the reaction mixture and 10 units of maltogenic α-amylase were added to the mixture every 3 hours, and the reaction was performed at 40° C. for a total of 24 hours.

Thereafter, the reaction product was subjected to gel filtration using Sephadex G-15, thereby obtaining about 30 mg of hydroquinone glycoside (purity 80%).

In the gel filtration, a fraction different from the one containing hydroquinone glycoside contained saccharides About 50% of the saccharides contained this saccharide-containing fraction was isomalto-oligosaccharide.

Example 6

Production of Catechin-O-α-D-glucopyranoside

Catechin (manufactured by Funakoshi Co., Ltd.) and maltopentaose (manufactured by Ensuiko Sugar Refining Co., Ltd.) were dissolved in 20 mM acetic acid-Na buffer solution (pH 5.5), thereby obtaining a solution containing 2% by weight catechin and 10% by weight maltopentaose. To 1 ml of this solution, 1 ml of an enzyme solution containing saccharifying amylase having cyclodextrin synthesizing capability with an amylase activity of 10 units was added, thereby obtaining a mixture. This enzyme solution had been prepared using *Bacillus subtilis* strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with acetonitrile/ethyl acetate/0.05% phosphoric acid=12/2/86. The product was detected by absorbance at 280 nm. As a result, a peak of catechin glycoside other than unreacted catechin was newly observed.

Further, 40 enzyme activity units of α-glucosidase (manufactured by Toyobo) was added to 2 ml of the reaction product. The mixture was allowed to react at 40° C. for 6 hours. α-glucosidase is an enzyme which hydrolyzes a α-D-glucoside linkage present at a non-reducing terminal. Thereafter, the reaction product was analyzed by HPLC in the same manner as described above. As a result, the peak of catechin glycoside disappeared, and the peak of unreacted catechin was increased as compared to the peak of the reaction product before the α-glucosidase treatment. As a result, it was confirmed that the catechin glycoside is a compound in which glucose is linked to catechin with an α-D-glucoside linkage. The glycosyl transfer rate of the reaction was about 28%.

The reaction product was fractioned with a cation exchange resin (manufactured by Mitsubishi Chemical Corporation; DIAION UBK530) using water as a mobile phase. As a result, purified catechin glycoside (5 mg) was obtained (purity 70%).

Example 7

Production of Epigallocatechin-O-α-D-glucopyranoside

Epigallocatechin (manufactured by Funakoshi Co., Ltd.) and maltopentaose (manufactured by Ensuiko Sugar Refining Co., Ltd.) were dissolved in 20 mM acetic acid-Na buffer solution (pH 5.5), thereby obtaining a solution containing 2% by weight epigallocatechin and 10% by weight maltopentaose. To 1 ml of this solution, 1 ml of an enzyme solution containing saccharifying amylase having cyclodextrin synthesizing capability with an amylase activity of 10 units was added, followed by stirring, thereby obtaining a mixture. This enzyme solution had been prepared using *Bacillus subtilis* strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with acetonitrile/ethyl acetate/0.05% phosphoric acid=12/2/86. The product was detected by absorbance at 280 nm. As a result, the peak of epigallocatechin glycoside other than unreacted epigallocatechin was newly observed.

Further, 40 enzyme activity units of α-glucosidase (manufactured by Toyobo) was added to 2 ml of the reaction product. The mixture was allowed to react at 40° C. for 6 hours. Thereafter, the reaction product was analyzed by HPLC in the same manner as described above. As a result, the peak of epigallocatechin glycoside disappeared, and the peak of unreacted epigallocatechin was increased as compared to the peak of the reaction product before the α-glucosidase treatment. As a result, it was confirmed that the epigallocatechin glycoside is a compound in which glucose is linked to epigallocatechin with an α-D-glucoside linkage. The glycosyl transfer rate of the reaction was about 20%.

The reaction product was fractioned with a cation exchange resin (manufactured by Mitsubishi Chemical Corporation; DIAION UBK530) using water as a mobile phase. As a result, purified epigallocatechin glycoside (7 mg) was obtained (purity 70%).

Example 8

Production of Epicatechin
Gallate-O-α-D-glucopyranoside

Epicatechin gallate (manufactured by Funakoshi Co., Ltd.) and maltopentaose (manufactured by Ensuiko Sugar Refining Co., Ltd.) were dissolved in 20 mM acetic acid-Na buffer solution (pH 5.5), thereby obtaining a solution containing 2% by weight epicatechin gallate and 10% by weight maltopentaose. To 1 ml of this solution, 1 ml of an enzyme solution containing saccharifying amylase having cyclodextrin synthesizing capability with an amylase activity of 20 units was added, followed by stirring, thereby obtaining a mixture. This enzyme solution had been prepared using *Bacillus subtilis* strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with acetonitrile/ethyl acetate/0.05% phosphoric acid=12/2/86. The product was detected by absorbance at 280 nm. As a result, the peak of epicatechin gallate glycoside other than unreacted epicatechin gallate was newly observed.

Further, 40 enzyme activity units of α-glucosidase (manufactured by Toyobo) was added to 2 ml of the reaction product. The mixture was allowed to react at 40° C. for 6 hours. Thereafter, the reaction product was analyzed by HPLC in the same manner as described above. As a result, the peak of epicatechin gallate glycoside disappeared, and the peak of unreacted epicatechin gallate was increased as compared to the peak of the reaction product before the α-glucosidase treatment. As a result, it was confirmed that the epicatechin gallate glycoside is a compound in which glucose is linked to epicatechin gallate with an α-D-glucoside linkage. The glycosyl transfer rate of the reaction was about 20%.

The reaction product was fractioned with a cation exchange resin (manufactured by Mitsubishi Chemical Corporation; DIAION SK1B) using water as a mobile phase. As a result, purified epicatechin gallate glycoside (8 mg) was obtained (purity 70%).

Example 9

Production of 3,4-dimethoxy
Phenol-O-α-D-glucopyranoside 3,4-dimethoxy phenol (manufactured by Sigma) and maltopentaose (manufactured by Ensuiko. Sugar Refining Co., Ltd.) were dissolved in 20 mM acetic acid-Na buffer solution (pH 5.5), thereby obtaining a solution containing 2% by weight 3,4-dimethoxyphenol and 10% by weight maltopentaose. To 1 ml of this solution, 1 ml of an enzyme solution containing saccharifying amylase having cyclodextrin synthesizing capability with 15 unit amylase activity was added, followed by stirring, thereby obtaining a mixture. This enzyme solution had been prepared using *Bacillus subtilis* strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with 25% methanol aqueous solution. The product was detected by absorbance at 280 nm. As a result, the peak of 3,4-dimethoxy phenol glycoside other than unreacted 3,4-dimethoxy phenol was newly observed.

Further, 40 enzyme activity units of α-glucosidase (manufactured by Toyobo) was added to 2 ml of the reaction product. The mixture was allowed to react at 40° C. for 4 hours. Thereafter, the reaction product was analyzed by HPLC in the same manner as described above. As a result, the peak of 3,4-dimethoxy phenol glycoside disappeared, and the peak of unreacted 3,4-dimethoxy phenol was increased as compared to the peak of the reaction product before the α-glucosidase treatment. As a result, it was confirmed that the 3,4-dimethoxy phenol glycoside is a compound in which glucose is linked to 3,4-dimethoxy phenol with an α-D-glucoside linkage. The glycosyl transfer rate of the reaction was about 12%.

The reaction product was fractioned with a cation exchange resin (manufactured by Mitsubishi Chemical Corporation; DIAION UBK530) using water as a mobile phase. As a result, purified 3,4-dimethoxy phenol glycoside (2 mg) was obtained (purity 90%).

Example 10

Production of 3,5-dimethoxy
Phenol-O-α-D-glucopyranoside 3,5-dimethoxy phenol (manufactured by Sigma) and maltopentaose (manufactured by Ensuiko Sugar Refining Co., Ltd.) were dissolved in 20 mM acetic acid-Na buffer solution (pH 5.5), thereby obtaining a solution containing 2% by weight 3,5-dimethoxy phenol and 10% by weight maltopentaose. To 1 ml of this solution, 1 ml of an enzyme solution containing saccharifying amylase having cyclodextrin synthesizing capability with an amylase activity of 15 units was added, followed by stirring, thereby obtaining a mixture. This enzyme solution had been prepared using *Bacillus* subtilis strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with 25% methanol aqueous solution. The product was detected by absorbance at 280 nm. As a result, the peak of 3,5-dimethoxy phenol glycoside other than unreacted 3,5-dimethoxy phenol was newly observed.

Further, 40 enzyme activity units of α-glucosidase (manufactured by Toyobo) was added to 2 ml of the reaction product. The mixture was allowed to react at 40° C. for 4 hours. Thereafter, the reaction product was analyzed by HPLC in the same manner as described above. As a result, the peak of 3,5-dimethoxy phenol glycoside disappeared, and the peak of unreacted 3,5-dimethoxy phenol was increased as compared to the peak of the reaction product before the α-glucosidase treatment. As a result, it was confirmed that the 3,5-dimethoxy phenol glycoside is a compound in which glucose is linked to 3,5-dimethoxy phenol with an α-D-glucoside linkage. The glycosyl transfer rate of the reaction was about 18%.

The reaction product was fractioned with a cation exchange resin (manufactured by Mitsubishi Chemical Corporation; DIAION UBK530) using water as a mobile phase. As a result, purified 3,5-dimethoxy phenol glycoside (4 mg) was obtained (purity 90%).

Example 11

Production of
Acetaminophen-O-α-D-glucopyranoside

Acetaminophen (manufactured by Sigma) and maltopentaose (manufactured by Ensuiko Sugar Refining Co., Ltd.) were dissolved in 20 mM acetic acid-Na buffer solution (pH 5.5), thereby obtaining a solution containing 2% by weight acetaminophen and 10% by weight maltopentaose. To 1 ml of this solution, 1 ml of an enzyme solution containing saccharifying amylase having cyclodextrin synthesizing capability with an amylase activity of 10 units was added, followed by stirring, thereby obtaining a mixture. This enzyme solution had been prepared using Bacillus subtilis strain IFO14140 by a method described in Okada et al. (supra). The mixture was allowed to react at 40° C. for 16 hours.

Thereafter, the reaction product was analyzed by HPLC. In the HPLC, ODS column RP-18 was used and elution was performed with 25% methanol aqueous solution. The product was detected by absorbance at 280 nm. As a result, the peak of acetaminophen glycoside other than unreacted acetaminophen was newly observed.

Further, 40 enzyme activity units of α-glucosidase (manufactured by Toyobo) was added to 2 ml of the reaction product. The mixture was allowed to react at 40° C. for 4 hours. α-glucosidase is an enzyme which hydrolyzes a α-D-glucoside linkage present at a non-reducing terminal. Thereafter, the reaction product was analyzed by HPLC in the same manner as described above. As a result, the peak of acetaminophen glycoside disappeared, and the peak of unreacted acetaminophen was increased as compared to the peak of the reaction product before the α-glucosidase treatment. As a result, it was confirmed that the acetaminophen glycoside is a compound in which glucose is linked to acetaminophen with an α-D-glucoside linkage. The glycosyl transfer rate of the reaction was about 5%.

The reaction product was fractioned with a cation exchange resin (manufactured by Mitsubishi Chemical Corporation; DIAION UBK530) using water as a mobile phase. As a result, purified acetaminophen glycoside (1 mg) was obtained (purity 85%).

Example 12

Production of
Hydroquinone-O-α-D-glucopyranoside

Hydroquinone (manufactured by Wako Pure Chemical Industries Ltd.) and maltopentaose (manufactured by Ensuiko Sugar Refining Co., Ltd.) were dissolved in 20 mM acetic acid-Na buffer solution (pH 5.5), thereby obtaining a solution containing 10% by weight hydroquinone and 10% by weight maltopentaose. To 10 ml of this solution, powdered saccharifying amylase having cyclodextrin synthesizing capability with an enzyme activity of 30 units was added, thereby obtaining a mixture. This powder was prepared using Bacillus subtilis IFO14140 by a method described in Okada et al. (supra). The mixture was allowed to react at 40° C., to which 1 g of maltopentaose and 30 units of saccharifying amylase having cyclodextrin synthesizing capability were further added based on the weight of the mixture 3, 9 and 15 hours after the start of the reaction. The reaction was performed for a total of 19 hours.

Thereafter, the reaction product was subjected to gel filtration using Sephadex G-25, thereby obtaining about 600 mg of hydroquinone monoglycoside (purity 96%).

Example 13

Production of
Hydroquinone-O-α-D-glucopyranoside

Hydroquinone (manufactured by Wako Pure Chemical Industries, Ltd.) and a starch degradation product (manufactured by Matsutani Chemical Industry Co., Ltd.; PINE-DEX 1) were dissolved in water, thereby obtaining a solution containing 15% by weight hydroquinone and 40% by weight starch degradation product. To 10 ml of this solution, powdered saccharifying amylase having cyclodextrin synthesizing capability with an enzyme activity of 30 units was added, followed by stirring, thereby obtaining a mixture. This powder had been prepared using Bacillus subtilis strain IFO14140 by a method described in Okada et al. (supra). The mixture was allowed to react at 40° C. for 20 hours.

Thereafter, the reaction product was fractioned with DIAION UBK530 manufactured by Mitsubishi Chemical Corporation using water as a mobile phase, thereby obtaining a fraction containing hydroquinone monoglucoside. The fraction was passed through DIAION PA308 to be decolored. As a result, about 1 g of hydroquinone monoglycoside was obtained (purity 95%).

Example 14

Large Scale Production of
Hydroquinone-O-α-D-glucopyranoside

Hydroquinone (manufactured by Wako Pure Chemical Industries, Ltd.) and a starch degradation product (manufactured by Matsutani Chemical Industry Co., Ltd.; PINE-DEX 100) were dissolved in water, thereby obtaining a solution containing 15% by weight hydroquinone and 40% by weight starch degradation product. To 10 liters of this solution, powdered saccharifying amylase having cyclodextrin synthesizing capability with an enzyme activity of 30,000 units was added, followed by stirring, thereby obtaining a mixture. This powder had been prepared using *Bacillus subtilis* strain IFO14140 by a method described in Okada et al. (supra). The mixture was allowed to react at 40° C. for 20 hours.

Thereafter, the reaction product was continuously fractioned by simulated moving bed column chromatography with DIAION UBK530 manufactured by Mitsubishi Chemical Corporation using water as a mobile phase, thereby obtaining a fraction containing hydroquinone monoglucoside. The fraction was passed through DIAION PA308 to be decolored. As a result, about 1 kg of hydroquinone monoglycoside was obtained (purity 98%).

Example 15

Production of Hydroquinone-O-α-D-glucopyranoside

Hydroquinone (manufactured by Wako Pure Chemical Industries, Ltd.) and a starch degradation product (manufactured by Sanwa Cornstarch Co., Ltd.; SUNDECK 70) were dissolved in water, thereby obtaining a solution containing 15% by weight hydroquinone and 40% by weight starch degradation product. To 10 ml of this solution, powdered saccharifying amylase having cyclodextrin synthesizing capability with an enzyme activity of 30 units was added, followed by stirring, thereby obtaining a mixture. This powder had been prepared using *Bacillus subtilis* IFO14140 by a method described in Okada et al. (supra). The mixture was allowed to react at 40° C. for 20 hours.

Thereafter, the reaction product was fractioned with Amberlite 1310Na (manufactured by Organo Corporation) using water as a mobile phase. As a result, about 1 g of hydroquinone monoglycoside was obtained (purity 96%).

Example 16

Large Scale Production of Hydroquinone-O-α-D-glucopyranoside

Hydroquinone (manufactured by Wako Pure Chemical Industries, Ltd.) and a starch degradation product (manufactured by Matsutani Chemical Industry Co., Ltd.; MAX 1000EX) were dissolved in water, thereby obtaining a solution containing 15% by weight hydroquinone and 40% by weight starch degradation product. To 10 liters of this solution, powdered saccharifying amylase having cyclodextrin synthesizing capability with an enzyme activity of 30,000 units was added, followed by stirring, thereby obtaining a mixture. This powder had been prepared using *Bacillus subtilis* strain IFO14140 by a method described in Okada et al. (supra). The mixture was allowed to react at 40° C. for 20 hours.

Thereafter, the reaction product was continuously fractioned by simulated moving bed chromatography with Amberlite 1310Na (manufactured by Organo Corporation) using water as a mobile phase, thereby obtaining a fraction containing hydroquinone monoglucoside. As a result, about 1 kg of hydroquinone monoglycoside was obtained (purity 94%).

Example 17

Production of Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid-Na buffer solution (pH 5.5), thereby obtaining a solution containing 5% by weight hydroquinone and 50% by weight maltopentaose. To 10 ml of this solution, 5 ml of an enzyme solution containing cyclomaltodextrinase having an enzyme activity of 20 units was added, followed by stirring, thereby obtaining a mixture. The enzyme solution was the *Alkalophilic Bacillus* sp. A2-5a-derived enzyme solution obtained in Production Example 1. The mixture was allowed to react at 40° C. for 16 hours.

Thereafter, the reaction product was fractioned by column chromatography with Amberlite 1310Na (manufactured by Organo Corporation) using water as a mobile phase. As a result, about 75 mg of hydroquinone glycoside was obtained (purity 80%).

In the column chromatography, a fraction different from one containing hydroquinone glycoside contained saccharides. About 50% of the saccharides contained in this saccharide-containing fraction was isomalto-oligosaccharide.

Example 18

Production of Hydroquinone-O-α-D-glucopyranoside

Hydroquinone (manufactured by Wako Pure Chemical Industries, Ltd.) and maltopentaose (manufactured by Ensuiko Sugar Refining Co., Ltd.) were dissolved in 20 mM acetic acid-Na buffer solution (pH 5.5), thereby obtaining a solution containing 3% by weight hydroquinone and 10% by weight maltopentaose. To 10 ml of this solution, 10 ml of a maltogenic α-amylase enzyme solution having an enzyme activity of 10 units was added, followed by stirring, thereby obtaining a mixture. The enzyme solution had been prepared by a method described in J. Biol. Chem. 267(31), 22108–22114, 1992, using *E. coli* deposited in National Institute of Bioscience and Human-Technology, Agency of Industrial Science and Technology (deposition number: FERM P-13717). This *E. coli* has the gene for *Thermoactinomyces vulgaris* R-47 strain-derived maltogenic α-amylase, and expresses that maltogenic α-amylase. Hydroquinone corresponding to 2% based on the weight of the mixture, maltopentaose corresponding 4% based on the weight of the mixture and 10 enzyme activity units of maltogenic α-amylase were added to the mixture every 3 hours, where the reaction was performed at 40° C. for a total of 24 hours.

Thereafter, the reaction product was fractioned by column chromatography with Amberlite 1310Na (manufactured by Organo Corporation) using water as a mobile phase. As a result, about 30 mg of hydroquinone glycoside was obtained (purity 96%).

In the column chromatography, a fraction, which was different from one containing hydroquinone glycoside contained saccharides, was obtained. About 50% of the saccharides contained in this saccharide-containing fraction was isomalto-oligosaccharide.

Example 19

Production of Hydroquinone-O-α-D-glucopyranoside

Hydroquinone (manufactured by Wako Pure Chemical Industries, Ltd.) and a starch degradation product (manufactured by Matsutani Chemical Industry Co., Ltd.; MAX 1000EX) were dissolved in water, thereby obtaining a solution containing 20% by weight hydroquinone and 50% by weight starch degradation product. To 10 liters of this solution, powdered saccharifying amylase having cyclodextrin synthesizing capability with an enzyme activity of 50,000 units was added, followed by stirring, thereby obtaining a mixture. This powder had been prepared using *Bacillus subtilis* strain IFO14140 by a method described in Okada et al. (supra). The mixture was allowed to react at 40° C. for 20 hours.

Thereafter, the reaction product was fractioned by column chromatography with DIAION WA-30 (manufactured by Mitsubishi Chemical Corporation) converted to Cl type by equilibration with HCl, using water as a mobile phase, thereby obtaining a fraction containing hydroquinone monoglucoside. As a result, about 1.2 kg of hydroquinone monoglycoside was obtained (purity 96%).

Example 20

Production of Hydroquinone-O-α-D-glucopyranoside

Hydroquinone (manufactured by Wako Pure Chemical Industries, Ltd.) and a starch degradation product (manufactured by Matsutani Chemical Industry Co., Ltd.; MAX 1000EX) were dissolved in water, thereby obtaining a solution containing 20% by weight hydroquinone and 50% by weight starch degradation product. To 10 liters of this solution, powdered saccharifying amylase having cyclodextrin synthesizing capability with an enzyme activity of 50,000 units was added, followed by stirring, thereby obtaining a mixture. This powder had been prepared using *Bacillus subtilis* strain IFO14140 by a method described in Okada et al. (supra). The mixture was allowed to react at 40° C. for 20 hours.

Thereafter, the reaction product was fractioned by column chromatography with DIAION PA-412 (manufactured by Mitsubishi Chemical Corporation) converted to Cl type by equilibration with HCl, using water as a mobile phase, thereby obtaining a fraction containing hydroquinone monoglucoside. As a result, about 1.0 kg of hydroquinone monoglycoside was obtained (purity 95%).

Example 21

Production of Hydroquinone-O-α-D-glucopyranoside Using *Bacillus subtilis* Strain K02

A reaction was conducted in the same manner as in Example 1, except that an enzyme solution containing saccharifying amylase having cyclodextrin synthesizing capability derived from *Bacillus subtilis* K02 described in Okada et al. (supra) was used instead of the enzyme solution containing *Bacillus subtilis* strain IFO14140-derived saccharifying amylase having cyclodextrin synthesizing capability. The enzyme solution had been prepared by a method described in Okada et al. (supra) using *Bacillus subtilis* strain K02.

To this reaction solution, 20 units of α-glucosidase (manufactured by Toyobo) was added, followed by incubation at 40° C. for 4 hours. After the incubation, the solution was subjected to HPLC with ODS column RP-18 (manufactured by Merck) using 20% methanol aqueous solution adjusted to pH 2.5 as a mobile phase. As a control, a solution without α-glucosidase treatment was also subjected to HPLC. The absorbance of each fraction of the eluate was measured at 280 nm, thereby detecting hydroquinone glycoside. As a result, when treated with α-glucosidase, the peak of hydroquinone monoglucoside completely disappeared and the peak of hydroquinone was increased, as compared to the untreated solution. Therefore, it was found that hydroquinone glycoside was also produced when strain K02 was used.

Moreover, from the HPLC elution time of the hydroquinone glycoside and the degradation of that due to using α-glucosidase, it was found that the glycoside is a glycoside in which glucose is linked to hydroquinone with an α linkage.

Example 22

Production of Hydroquinone-O-α-D-glucopyranoside Using *Bacillus subtilis* Strain K05

A reaction was conducted in the same manner as in Example 1, except that an enzyme solution containing saccharifying amylase having cyclodextrin synthesizing capability derived from *Bacillus subtilis* strain K05 described in Okada et al. (supra) (the enzyme solution was prepared by a method described in Okada et al. (supra)) was used instead of the enzyme solution containing *Bacillus subtilis* strain IFO14140-derived saccharifying amylase having cyclodextrin synthesizing capability. The enzyme solution had been prepared by a method described in Okada et al. (supra) using *Bacillus subtilis* strain K05.

To this reaction solution, 20 units of α-glucosidase (manufactured by Toyobo) was added, followed by incubation at 40° C. for 4 hours. After the incubation, the solution was subjected to HPLC with ODS column RP-18 (manufactured by Merck) using 20% methanol aqueous solution adjusted to pH 2.5 as a mobile phase. As a control, a solution without α-glucosidase treatment was also subjected to HPLC. The absorbance of each fraction of the eluate was measured at 280 nm, thereby detecting hydroquinone glycoside. As a result, when treated with α-glucosidase, the peak of hydroquinone monoglucoside completely disappeared and the peak of hydroquinone was increased, as compared to the untreated solution. Therefore, it was found that hydroquinone glycoside was also produced when strain K05 was used.

Example 23

Production of Hydroquinone-O-α-D-glucopyranoside Using *Bacillus subtilis* Strain K12

A reaction was conducted in the same manner as in Example 1, except that an enzyme solution containing saccharifying amylase having cyclodextrin synthesizing capability derived from *Bacillus subtilis* K12 described in Okada et al. (supra) (the enzyme solution was prepared by a method described in Okada et al. (supra)) was used instead of the enzyme solution containing *Bacillus subtilis* strain IFO14140-derived saccharifying amylase having cyclodextrin synthesizing capability. The enzyme solution had been prepared by a method described in Okada et al. (supra) using *Bacillus subtilis* strain K12.

To this reaction solution, 20 units of α-glucosidase (manufactured by Toyobo) was added, followed by incubation at 40° C. for 4 hours. After the incubation, the solution was subjected to HPLC with ODS column RP-18 (manufactured by Merck) using 20% methanol aqueous solution adjusted to pH 2.5 as a mobile phase. As a control, a solution without α-glucosidase treatment was also subjected to HPLC. The absorbance of each fraction of the eluate was measured at 280 nm, thereby detecting hydroquinone glycoside. As a result, when treated with α-glucosidase, the peak of hydroquinone monoglucoside completely disappeared and the peak of hydroquinone was increased, as compared to the untreated solution. Therefore, it was found that hydroquinone glycoside was also produced when strain K12 was used.

Example 24

Production of
Hydroquinone-O-α-D-glucopyranoside Using
*Bacillus subtilis* Strain D11

A reaction was conducted in the same manner as in Example 1, except that an enzyme solution containing saccharifying amylase having cyclodextrin synthesizing capability derived from *Bacillus subtilis* strain D11 described in Okada et al. (supra) (the enzyme solution was prepared by a method described in Okada et al. (supra)) was used instead of the enzyme solution containing *Bacillus subtilis* strain IFO14140-derived saccharifying amylase having cyclodextrin synthesizing capability. The enzyme solution had been prepared by a method described in Okada et al. (supra) using *Bacillus subtilis* strain D11.

To this reaction solution, 20 units of α-glucosidase (manufactured by Toyobo) was added, followed by incubation at 40° C. for 4 hours. After the incubation, the solution was subjected to HPLC with ODS column RP-18 (manufactured by Merck) using 20% methanol aqueous solution adjusted to pH 2.5 as a mobile phase. As a control, a solution without α-glucosidase treatment was also subjected to HPLC. The absorbance of each fraction of the eluate was measured at 280 nm, thereby detecting hydroquinone glycoside. As a result, when treated with α-glucosidase, the peak of hydroquinone monoglucoside completely disappeared and the peak of hydroquinone was increased, as compared to the untreated solution. Therefore, it was found that hydroquinone glycoside was also produced when strain D11 was used.

INDUSTRIAL APPLICABILITY

The present invention provides a method of producing a phenol derivative glycoside. In the present invention, neopullulanase, cyclomaltodextrinase, maltogenic α-amylase or saccharifying amylase having cyclodextrin synthesizing capability undergoes glycosyl transfer via an a linkage for a phenol derivative, such as hydroquinone, catechin, and epigallocatechin.

When neopullulanase, cyclomaltodextrinase, or maltogenic α-amylase is used, isomalto-oligosaccharide as well as glycoside can be simultaneously obtained.

The invention claimed is:

1. A method of producing a phenol derivative glycoside, comprising the step of allowing a saccharide and a phenol derivative to react with each other in the presence of an enzyme to produce the phenol derivative glycoside, wherein the enzyme is selected from the group consisting of neopullulanase, cyclomaltodextrinase, maltogenic .alpha.-amylase, and saccharifying amylase having cyclodextrin synthesizing capability.

2. A method according to claim 1, wherein the enzyme is neopullulanase, and the neopullulanase is derived from a *bacterium* selected from the group consisting of *Thermoactinomyces vulgaris, Bacteroides thetaiotaom icron, Pseudomonas, Bacillus polymyxa, Bacillus licheniformis, Bacillus stearothermophilus, Bacillus thermoamyloliquefaciens*, and *Thermus thermophilus*.

3. A method according to claim 1, wherein the enzyme is cyclomaltodextrinase, and the cyclomaltodextrinase is derived from a *bacterium* selected from the group consisting of *Bacillus stearothermophilus, Bacillus thermophilus, Bacillus coagulanc, Escherichia coli, Flavobacterium, Alkalophic Bacillus*, and *Bacillus sphaericus*.

4. A method according to claim 1, wherein the enzyme is maltogenic .alpha.-amylase, and the maltogenic .alpha.-amylase is derived from a *bacterium* selected from the group consisting of *Thermoactinomyces vulgaris, Bacteroides thetaiotaomicron, Pseudomonas, Bacillus polymyxa, Bacillus licheniformis, Bacillus stearothermophilus, Bacillus thermoamyloliquefaciens*, and *Thermus thermophilus*.

5. A method according to claim 1, wherein the enzyme is a saccharifying amylase having cyclodextrin synthesizing capability, and the saccharifying amylase having cyclodextrin synthesizing capability is derived from a *bacterium* selected from the group consisting of *Bacillus subtilis, Streptococcus bovis, Streptomyces hygroscopicus, Streptomyces praecox, Rhizopus delemar, Aspergillus delemar*, and *Aspergillus niger*.

6. A method according to claim 1, wherein the phenol derivative is selected from the group consisting of flavone-type compounds, isoflavone-type compounds, flavonol-type compounds, flavanone-type compounds, flavanonol-type compounds, catechin-type compounds, aurone-type compounds, chalcone-type compounds, dihydrochalcone-type compounds, kojic acid, dimethoxy phenol, acetaminophen, vanillin, hydroquinone, epigallocatechin, epicatechin gallate, anthocyanidin-type compounds, anthocyanin-type compounds, caffeic acid, catechol, resorcinol, protocatechuic acid, gallic acid, resorcylic acid, and phloroglucinol.

7. A method according to claim 1, wherein the saccharide is selected from the group consisting of malto-oligosaccharides, dextrin, amylose,
   amylopectin, natural starch, starch degradation products and processed starch.

8. A method according to claim 1, further comprising the step of using ion exchange resin to fractionate the enzyme reaction products.

9. A method according to claim 1, further comprising the step of using ion exchange resin to fractionate the enzyme reaction products into at least a fraction containing a byproduct, a fraction containing an unreacted phenol derivative,
   and a fraction containing a phenol derivative glycoside.

* * * * *